US010502672B2

(12) United States Patent
Siedel et al.

(10) Patent No.: US 10,502,672 B2
(45) Date of Patent: Dec. 10, 2019

(54) METHODS OF DETERMINING THE PROPERTIES OF A FLUID BODY

(71) Applicant: The Provost, Fellows, Foundation Scholars, & the Other Members of Board, of the College of the Holy, Dublin (IE)

(72) Inventors: Samuel Siedel, Laytown Co. Meath (IE); Anthony James Robinson, Laytown (IE)

(73) Assignee: The Provost, Fellows, Foundation Scholars, & the Other Members of Board, of the College of the Holy & Un-Div. Trinity of Queen Elizabeth Near Dublin, Dublin (IE)

( * ) Notice: Subject to any disclaimer, the term of this patent is extended or adjusted under 35 U.S.C. 154(b) by 92 days.

(21) Appl. No.: 15/519,127

(22) PCT Filed: Oct. 14, 2015

(86) PCT No.: PCT/EP2015/073806
§ 371 (c)(1),
(2) Date: Apr. 13, 2017

(87) PCT Pub. No.: WO2016/059124
PCT Pub. Date: Apr. 21, 2016

(65) Prior Publication Data
US 2017/0227435 A1 Aug. 10, 2017

(30) Foreign Application Priority Data
Oct. 14, 2014 (EP) .................................. 14188853

(51) Int. Cl.
G01N 13/02 (2006.01)

(52) U.S. Cl.
CPC ..... *G01N 13/02* (2013.01); *G01N 2013/0241* (2013.01); *G01N 2013/0283* (2013.01)

(58) Field of Classification Search
CPC .............. G01N 2013/0241; G01N 2013/0283
See application file for complete search history.

(56) References Cited

U.S. PATENT DOCUMENTS

| 4,416,148 A | 11/1983 | Klus et al. | |
| 6,438,261 B1 * | 8/2002 | Moshe | G01N 15/1475 382/133 |

(Continued)

FOREIGN PATENT DOCUMENTS

JP 2009036634 A 2/2009

OTHER PUBLICATIONS

Lesage et al., Analysis of quasi-static vapour bubble shape during growth and departure. Physics of Fluids. 2013;25:067103.

(Continued)

Primary Examiner — Matthew G Marini
(74) Attorney, Agent, or Firm — Mintz Levin Cohn Ferris Glovsky and Popeo, P.C.

(57) ABSTRACT

The properties of a fluid body in the form of a surface-attached droplet/bubble can be determined. A data set is stored describing a plurality of droplets/bubbles of different shapes; each shape is captured as a combination of two or more linear dimensional measurements. For each shape the data set includes one or more parameters describing the relationship between the physical properties of a pair of fluids capable of forming that shape as a surface-attached droplet/bubble disposed in a surrounding fluid medium. A fluid body is provided in the form of a surface-attached droplet/bubble and a plurality of linear dimensional measurements are taken and provided as input to a processing apparatus. Processing apparatus determines from the data set (Continued)

the one or more parameters associated with the shape described by said linear dimensional measurements. Particular the surface tension of a fluid can be found in this way based on simple dimensional measurements.

19 Claims, 16 Drawing Sheets

(56) References Cited

U.S. PATENT DOCUMENTS

| | | | |
|---|---|---|---|
| 6,577,700 B1 * | 6/2003 | Fan | G01N 27/24 324/686 |
| 6,873,725 B2 * | 3/2005 | Xu | G01N 15/147 356/335 |
| 8,254,657 B2 * | 8/2012 | Pollack | G01N 15/1463 382/100 |

OTHER PUBLICATIONS

Lesage et al., Experimental and numerical analysis of quasi-static bubble size and shape characteristics at detachment. International Journal of Heat and Mass Transfer. 2013;64:53-69.

* cited by examiner

METHODS OF DETERMINING THE PROPERTIES OF A FLUID BODY

CROSS REFERENCE TO RELATED APPLICATIONS

This application is a national stage application filed under 35 U.S.C. I 371, of International Patent Application No. PCT/EP2015/073806, filed Oct. 14, 2015, which claims the benefit of and priority to European Patent Application No. 14188853.7, filed Oct. 14, 2014, the contents of each of which are incorporated by reference herein in its entirety.

TECHNICAL FIELD

This invention related to the determination of physical or thermodynamic properties of fluids.

It has particular application to determining properties which are measurable in respect of a first fluid when disposed within a surrounding fluid in the form of a droplet or bubble. Examples of such properties include surface tension, Bond number (and similar dimensionless characteristic numbers such as the Eötvös, Goucher, and Deryagin numbers), and density difference between phases, as wells as characteristics of the droplet or bubble including its volume, height, maximum width, base width, height of centre of gravity, apex curvature radius, interface area, base contact angle and capillary length. Since certain of these properties result from the effect of external fields and forces on a fluid (e.g. gravitational and other accelerating fields, electromagnetic fields etc., the method has application also in measuring such fields and forces.

BACKGROUND ART

The measurement of the properties of a fluid, such as its surface tension in a surrounding liquid or gas, is needed in many applications and across many industries including the food, textile, chemical, oil, pharmaceutical, biological and electronic industries, and in research institutions working in these fields. Similar to the surface tension measurement, other geometric properties of a bubble or drop can be measured using the same methodology, such as the bubble/drop volume, interface area, apex curvature radius, or height of centre of gravity. The angle at the base of the bubble/drop (known as contact angle) can also be measured similarly. This latter measurement is particularly useful in measuring the wettability property between a solid surface and a fluid; something that is vital in many engineering applications.

A common method of estimating surface tension involves accurately measuring and analysing the shape of a drop (or bubble) of the fluid. This shape is defined mathematically by a complex differential equation that involves the surface tension property as well as the respective fluid densities and gravity, which can be measured in other ways or looked up from a table of known values. By regression fitting a numerically integrated mathematical solution of the equation to the experimentally measured shape of the drop, the value of the surface tension is calculated.

FIG. 1 shows an experimental set-up for measuring the surface tension of an unknown transparent liquid 10. A gas bubble 12 is formed from an upward-facing horizontal orifice of a needle 14 of a syringe 16 into the unknown liquid 10. The bubble 12 is slowly and steadily injected, or simply steadily attached to the rim of the orifice, so that its shape corresponds to a static bubble shape. A camera 18 is used to capture the image of the bubble shape, illuminated by a backlight 20.

FIG. 2 shows an image captured from such a system. Image processing software can extract from this image a curve which approximates the profile of the bubble-liquid interface, subject to the constraints of the camera resolution and difference between the actual profile when viewed in a true mathematical elevation versus that captured by a camera capturing the bubble from a viewing angle that cannot quite see both opposite edges of the profile From a physical point of view, the shape of such an axisymmetric bubble is a result of the hydrostatic pressure gradients in both the liquid and gas phases and of the capillary equilibrium at the liquid-gas interface. The mathematical equation of the bubble profile can be written as follows (see F. J. Lesage, J. S. Cotton and A. J. Robinson, Analysis of quasi-static vapour bubble shape during growth and departure, Physics of Fluids, Vol. 25, p. 067103, 2013):

$$\frac{(\rho_l - \rho_g)g}{\sigma} z = \frac{2}{R_0} - C(z) \qquad \text{Eq. 1}$$

In equation 1, $\rho_l$, $\rho_g$ and $\sigma$ are properties of the fluid, respectively the liquid and gas densities and the interfacial surface tension; g is the gravitational acceleration; $R_0$ is the radius of curvature at the apex of the bubble; z is the vertical coordinate, downward from the apex of the bubble, and C is the curvature of the interface, which depends on the vertical coordinate (thus expressed as C(z)). The profile of the bubble is fully defined by this equation, and is cut by a horizontal plane which is the horizontal surface on which the bubble is attached.

More generally, the terms $\rho_l$, $\rho_g$ can be replaced by the densities of any two fluids and are not necessarily those of a liquid and a gas. Equation 1 can therefore be understood as covering the more general case of two fluids, not necessarily a liquid and a gas.

The interfacial surface tension, $\sigma$, is a property of the two fluids at the interface and therefore will be different for e.g. a water droplet in a heavy oil medium than it will for water in a gaseous medium. While interfacial surface tension is strictly speaking thus a property of the liquid and the gas, all gases effectively behave the same way, and so in the specific case of a liquid/gas interaction the surface tension is generally considered as a property specific to the liquid.

This equation is based on the assumption that the bubble or droplet is not freely floating but rather is attached to a surface. (Note that droplets and bubbles are, for these purposes, different examples of the same phenomenon, namely a discrete body of a first fluid disposed in a second fluid.) The droplet/bubble can be gravitationally accelerated, due to weight and buoyancy forces arising from the density difference with the surrounding fluid, either towards the surface in question, in which case it is a "sessile" droplet or bubble; or away from the surface, in which case it is a "pendant" droplet or bubble, remaining attached by surface tension forces that oppose the gravitationally-induced buoyancy or weight.

The bubble shown in FIG. 1 is pendant, and is equivalent to the classic image of a droplet of water hanging from a tap (or faucet) prior to it breaking off when it grows beyond the size limit allowing it to remain attached under surface tension. An example of a sessile droplet is a bead of water lying on a polished surface, while sessile bubbles would include bubbles of air trapped under a submerged glass surface. Note that while these simple examples all presume a liquid-gas or gas-liquid system of two fluids, the concepts apply equally to any two immiscible fluids of different densities. The bodies of a first fluid disposed in a second fluid will be referred to herein as droplets/bubbles, droplets, or bubbles, depending on context, it being appreciated that the terms can be used interchangeably from the point of view of the physics involved.

Equation 1 therefore provides a relation that links different properties of the two fluids and the gravitational acceleration to the geometry of the droplet/bubble. Thus, if sufficient independent parameters are known or measured, the other parameters can be deduced using this equation.

The usual way of calculating the surface tension of a fluid is as follows. The gravitational acceleration and the fluid densities are considered as known (or measured with a different method). Then, different geometrical profiles corresponding to equation 1 are generated by numerical integration of equation 1. Each numerical integration provides a solution which describes the entire surface of the bubble; from the base to the tip. A regression algorithm is utilized to obtain the solution that best fits the experimental profile, which is obtained by image processing. The best fitting profile provides the value of the surface tension property.

Similarly, the volume of the drop or bubble, or the height/position of its centre of gravity can be calculated when a best fit geometric profile is obtained describing the curvature of the profile.

Such methods have the drawback that they require significant image processing capability and mathematical computational power, as well as a good deal of post-processing time to obtain a good fit between the mathematical model and the experimental image.

DISCLOSURE OF THE INVENTION

There is provided a method of determining the properties of a fluid body in the form of a surface-attached droplet/bubble, comprising the steps of:
(a) storing, in a memory accessible by a processing apparatus, a set of data describing a plurality of droplets/bubbles of different shapes, wherein each shape is captured in said data set as a combination of two or more linear dimensional measurements, and wherein for each shape the data set includes one or more parameters describing the relationship between the physical properties of a pair of fluids capable of forming said shape when a first of said fluids is a surface-attached droplet/bubble disposed in a surrounding medium of the second of said fluids;
(b) providing a fluid body as a surface-attached droplet/bubble of a first fluid in a surrounding medium of a different second fluid;
(c) measuring a plurality of linear dimensional measurements of said fluid body;
(d) providing said measurements as an input to the processing apparatus; and
(e) said processing apparatus determining from said data set said one or more parameters associated with the shape described by said linear dimensional measurements.

The number of linear dimensions is specified as two or more. A third linear dimension may be required, depending on the dynamics of the system. For example, a bubble/drop issuing from an orifice of fixed dimension, which does not spread beyond the orifice, may have an implicit base diameter which can be built into the model or data set. Similarly a highly wetting fluid on a surface may result in a triple contact line of fixed dimension, reducing the number of required linear dimensions to specify a particular bubble/drop volume and shape to two.

It has been found that a set of data can be generated which characterises a family or universe of droplet/bubble shapes, where each such shape is defined using a combination of at least two linear measurements. Those linear measurements uniquely specify a shape from among the range of possible shapes, and the shape in turn is (based on a consideration of equation 1) attributable to the properties of the two fluids involved and the gravitational force. Accordingly, the experimental measurement of the required two linear dimensions of a particular bubble allows the shape, and the physical parameters associated with that shape, to be pinpointed in the data set.

This means that the determination of a physical property such as surface tension, can be obtained by modelling a universe of droplets/bubbles, where each is characterised by a pair of linear measurements, and then when it is desired to find the surface tension of a fluid one can simply make a couple of accurate linear measurements and look up the surface tension.

There are significant advantages with this method. Measurement of the linear dimensions of a droplet/bubble can be performed accurately without sophisticated image processing software. This makes this method suitable for implementation in a device which may not have sophisticated imaging or processing power, such as with the camera on a smartphone. Because the method involves a couple of linear measurements and a look-up operation, it can be performed in real time, unlike a curve-fitting exercise as in known methods. Linear dimensions can be measured with a higher degree of accuracy compared with regression fitting solutions of a numerical integration to a complex shape. Consequently, a higher accuracy may be reached using this method to measure surface tension.

It is not limited to surface tension. Once a droplet/bubble's shape has been modelled, it is possible to store, for that bubble, not only surface tension but also several other parameters which are specified once the shape is determined, e.g. volume, height of centre of gravity, contact angle, interface area, or capillary length. Accordingly the measurement of a pair of linear dimensions of a bubble and the provision of a data set in which bubbles are categorised and identified according to those measurements, allows the rapid and accurate determination of a number of complex physical parameters which were previously obtainable only with difficulty.

Preferably, one of the first and second fluids is known and the other is unknown, and the properties of the known fluid permit the derivation from said one or more parameters of corresponding properties of the unknown fluid.

This will often be the case in an experimental or real-world industrial set-up. The unknown fluid will be provided as a droplet/bubble in a fluid whose properties are completely known, such as water or air; or alternatively, the unknown fluid can be studied by introducing into it a bubble or droplet of e.g. air, water or a water-immiscible liquid such as toluene.

Preferably, said one or more parameters comprise a parameter which is a function of an accelerating field, a surface tension of one fluid at the interface with the other fluid, and the respective fluid densities.

Preferably, the accelerating field is the local gravitational field as characterised by the acceleration due to gravity, g. It can be envisaged however that applications will arise in which there is no local gravitational field, or in which the gravitational acceleration is supplemented by another external accelerating field. Such accelerations will influence the shape of any droplet or bubble. Similarly other external fields and forces can be taken into account including electromagnetic forces acting on the fluid.

Preferably, the two or more linear dimensional measurements are normalised measurements.

Further, preferably, the two or more linear measurements are normalised against a further linear measurement of the bubble/drop.

This is particularly useful as a method of standardising the data set. It also allows a dimension which is kept constant in the system to be used as a normalising dimension.

Preferably, the further linear measurement is a base diameter or base radius of the bubble drop at a surface to which it is attached.

Preferably, the two or more linear dimensional measurements of the data set comprise any two of the following measurements normalised against the remaining measurement: height normal to attachment surface, maximum width parallel to attachment surface, and base diameter (or radius) at attachment surface.

Optionally, the two or more linear dimensions of the data set may be expressed as a combination of dimensions such as an area or a volume.

Preferably, the data set is limited based on one or more of the following assumptions used to create the data set:
  a value for one or more properties of the first fluid;
  a value for one or more properties of the second fluid;
  a value for one or more properties of the interface between first and second fluids
  a value for an acceleration such as gravitational acceleration, g.

In this way, the data set can be simpler, i.e. the number of droplet/bubble shapes can be greatly compressed if assumptions are made, such as (most commonly) the value of the gravitational acceleration, but also possibly the data set may be tailored to identifying e.g. the surface tension of an unknown liquid by looking at the shape of an air bubble within that liquid, in which case the density of the air is known. Other simplifying assumptions can be made in other scenarios to reduce the complexity of the data set. Since the surface tension may be unique to the liquid, this provides a potential method of identifying a liquid.

Preferably, said set of data comprises a plurality of parameter sets, each parameter set describing a unique solution to an equation modelling the shape of a droplet/bubble, and each parameter set including said combination of two or more linear dimensional measurements and said one or more parameters describing the relationship between the physical properties of a pair of fluids capable of providing said solution.

There is also provided a method of obtaining the interfacial surface tension between a liquid in a gas, comprising the steps of:
  performing any of the methods as set out in the above statements of invention using a bubble of said gas in said liquid or a droplet of said liquid in said gas in step (b),
  wherein the resultant shape of the bubble/droplet is encompassed within the data set in step (a),
  wherein the one or more parameters describing the relationship between the physical properties of a pair of fluids include at least one parameter based on interfacial surface tension, said at least one parameter being determined in step (e).

There is also provided a computer program product comprising a set of instructions, which are effective to cause a processor to:
(a) receive as an input a plurality of linear dimensional measurements of a droplet/bubble;
(b) access a memory storing a set of data describing a plurality of droplets/bubbles of different shapes, wherein each shape is captured in said data set as a combination of two or more linear dimensional measurements, and wherein for each shape the data set includes one or more parameters describing the relationship between the physical properties of a pair of fluids capable of forming said shape when a first of said fluids is a surface-attached droplet/bubble disposed in a surrounding medium of the second of said fluids;
(c) determining from said data set said one or more parameters associated with the shape described by said linear dimensional measurements received as an input; and
(d) providing as an output said one or more parameters.

There is also provided an apparatus for determining the properties of a fluid body in the form of a surface-attached droplet/bubble, comprising:
(a) a memory storing a set of data describing a plurality of droplets/bubbles of different shapes, wherein each shape is captured in said data set as a combination of two or more linear dimensional measurements, and wherein for each shape the data set includes one or more parameters describing the relationship between the physical properties of a pair of fluids capable of forming said shape when a first of said fluids is a surface-attached droplet/bubble disposed in a surrounding medium of the second of said fluids;
(b) a processor programmed to receive as an input, a plurality of linear dimensional measurements of a fluid body as a surface-attached droplet/bubble of a first fluid in a surrounding medium of a different second fluid providing said measurements as an input to a processing apparatus; and
(c) a program causing said processor to determine from said data set said one or more parameters associated with the shape described by said linear dimensional measurements.

Preferably, the apparatus further comprises a measurement system for making said plurality of linear dimensional measurements, and an output therefrom to said processor The measurement system may comprise an optical sensor and imaging software calibrated to determine linear measurements of key parameters of a droplet/bubble whose image is captured by the optical sensor.

More preferably, the measurement system comprises a laser source and a detector for determining interception of a laser beam by an edge of a droplet.

Preferably, the apparatus further comprises means for introducing said droplet/bubble into said surrounding medium.

DETAILED DESCRIPTION OF PREFERRED EMBODIMENTS

Figure 1:
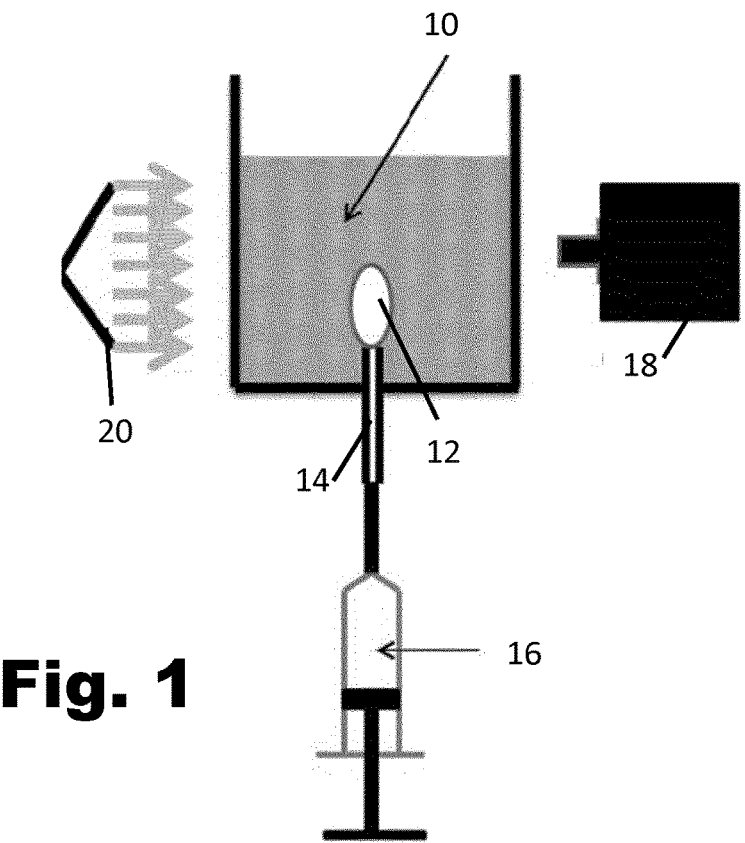
FIG. 1 is a diagram of an experimental set-up for measuring the surface tension of an unknown transparent liquid.
Figure 2:
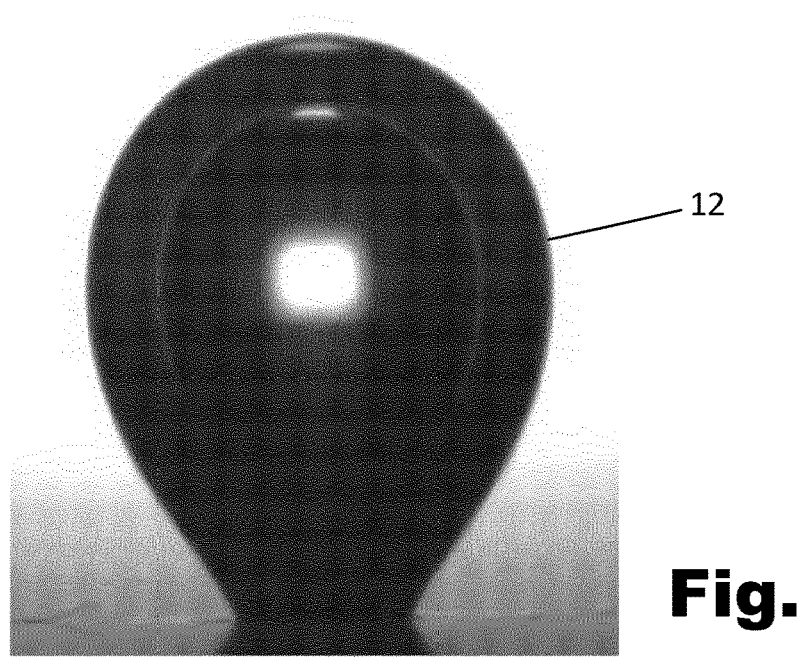
FIG. 2 is an image of a bubble of gas within a liquid, captured from the set-up of FIG. 1.
Figure 3:
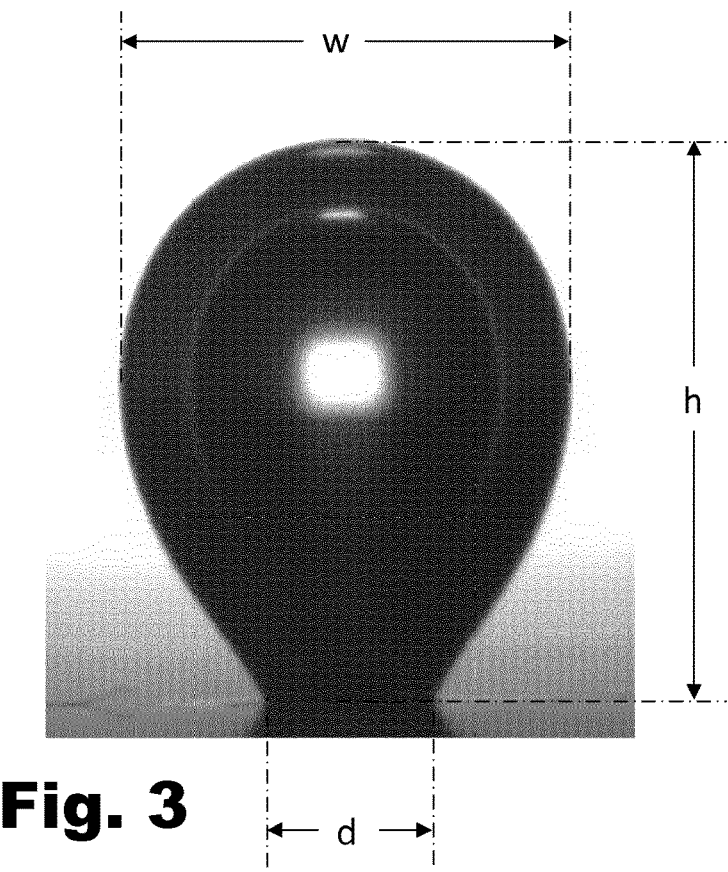
FIG. 3 shows the measurement of dimensions on the image of FIG. 2.

FIG. 3 shows the measurement of three linear dimensions of the bubble of FIG. 2, namely the bubble's maximum width w, its height h, and its base diameter, d. The base diameter is determined in this case by the orifice of the needle from which the air bubble has issued, and the width and height are functions not only of the volume of air that has been injected through the needle but also of the gravitational force g, the surface tension of the liquid into which the bubble is injected σ, and the respective densities of the two fluids. Accordingly, the same volume of a first fluid provided as a droplet or bubble in a surrounding second fluid can take up different shapes.

The shape of a bubble changes as the bubble grows. Equation 1 defines, for each pair of liquids in a given gravitational field (thus with, $\rho_l$, $\rho_g$, g and σ fixed) a unique curvature or capillary profile C(z) where the actual shape of the bubble or drop is determined by the height at which this profile is cut by the surface to which it is attached.

Figure 4:
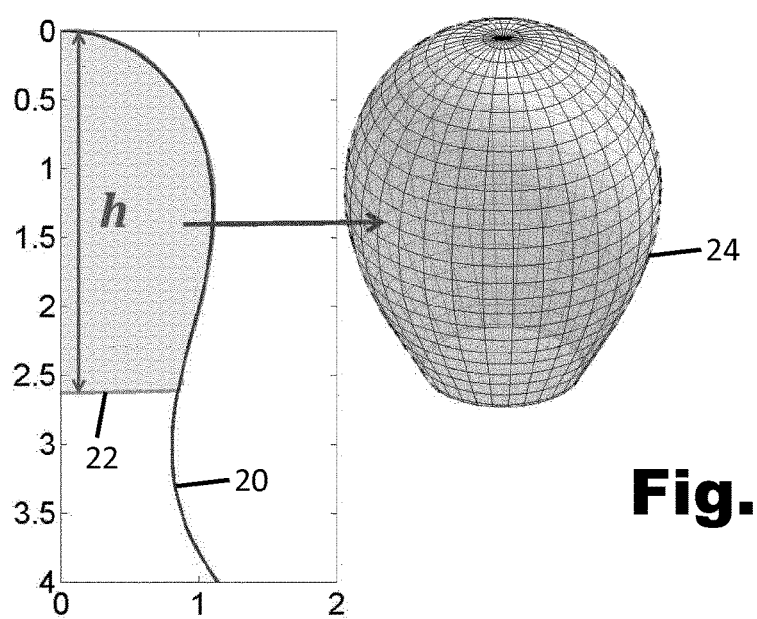
FIG. 4 is a diagram of a capillary profile mapped against height (y-axis) and width (x-axis) scales.

To illustrate this point, FIG. 4 shows a capillary profile 20 mapped against height (y-axis) and width (x-axis) scales of arbitrary units (in this figure, the dimensions are normalized by the radius of curvature at the apex). The profile can be cut by a surface 22 anywhere along its height h, giving rise to a corresponding bubble shape 24 which is defined by the profile and the height.

Figure 5:
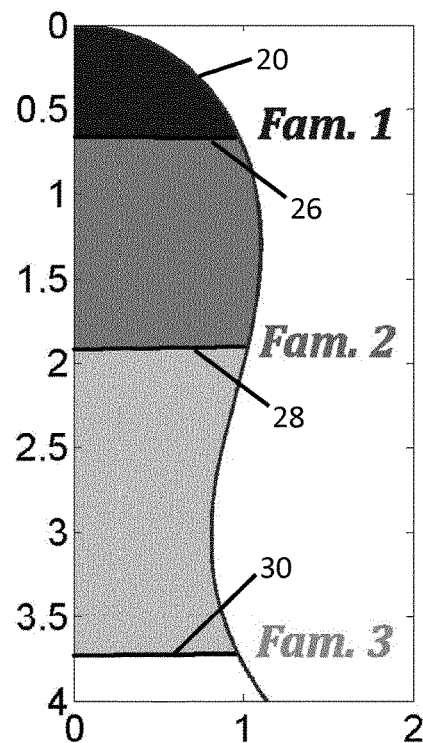
FIG. 5 is a capillary profile showing bubble families existing at different heights.

FIG. 5 shows that the same profile 20 can be cut by up to three different surfaces 26, 28, 30 with the same radius (or base diameter) giving rise to different bubble shapes. It is useful to consider three different families of bubble shapes, where the order of the family describes the number of changes of the slope of the bubble profile. From the apex to the base, the radius is always increasing for Family 1, the radius then decreases for Family 2 and a neck is formed for Family 3.

The curvature of the profile in FIG. 5 is merely one example of how a bubble or droplet may be shaped. Depending on the competing influences of gravity and surface tension, the shape may be quite different. A useful quantity to consider as a descriptor of the shape is the Bond number, Bo. Bond number is a dimensionless property of a fluid, defined as the square of the inverse of the capillary length, normalized by the square of the characteristic length. It captures, for a droplet/bubble, the density difference between the fluids, the gravitational acceleration, and the surface tension. Bond number can be considered as a measure of the importance of surface tension forces compared to body forces. A high Bond number indicates that the system is relatively unaffected by surface tension effects; a low number indicates that surface tension dominates. Intermediate numbers indicate a non-trivial balance between the two effects.

Figure 6:
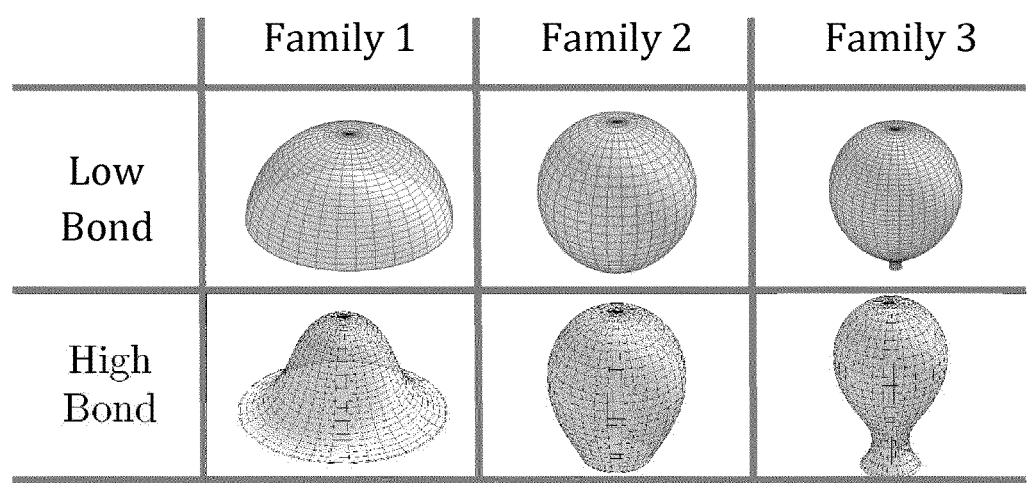
FIG. 6 is a graphical table showing six different droplet/bubble shapes.

FIG. 6 is a graphical table showing six different droplets/bubbles. There are two bubbles in each of the families 1, 2 and 3 described above. One bubble in each family (top row) is a shape resulting from a low Bond number while the other (bottom row) is a high Bond number shape. From this it can be seen that Bond number has a profound impact on droplet/bubble shape; or to be more accurate, the physical parameters of the liquids which underlie the Bond number have such an impact, which is handily captured by the Bond number as a single dimensionless parameter which is characteristic of the droplet/bubble shape and of the underlying parameters of the liquid.

In the present innovative method, a large number of solutions to equation 1 are numerically computed a priori, and the solutions are stored in a database. These solutions preferably cover the whole spectrum of bubble shapes that may be encountered. The solutions are numerically treated, in order to extract key geometrical features. In particular, key lengths such as bubble base radius, bubble height and bubble maximum width are calculated. Within certain conditions, a given set of these three linear lengths is sufficient to identify a unique bubble shape solution.

Using the bubble of the case of study, the three lengths can be measured very easily and nearly instantaneously. Importantly, it can be done very accurately as it does not rely on the use of sophisticated image processing, mathematical development or regression analysis (see FIG. 3).

Figure 7:
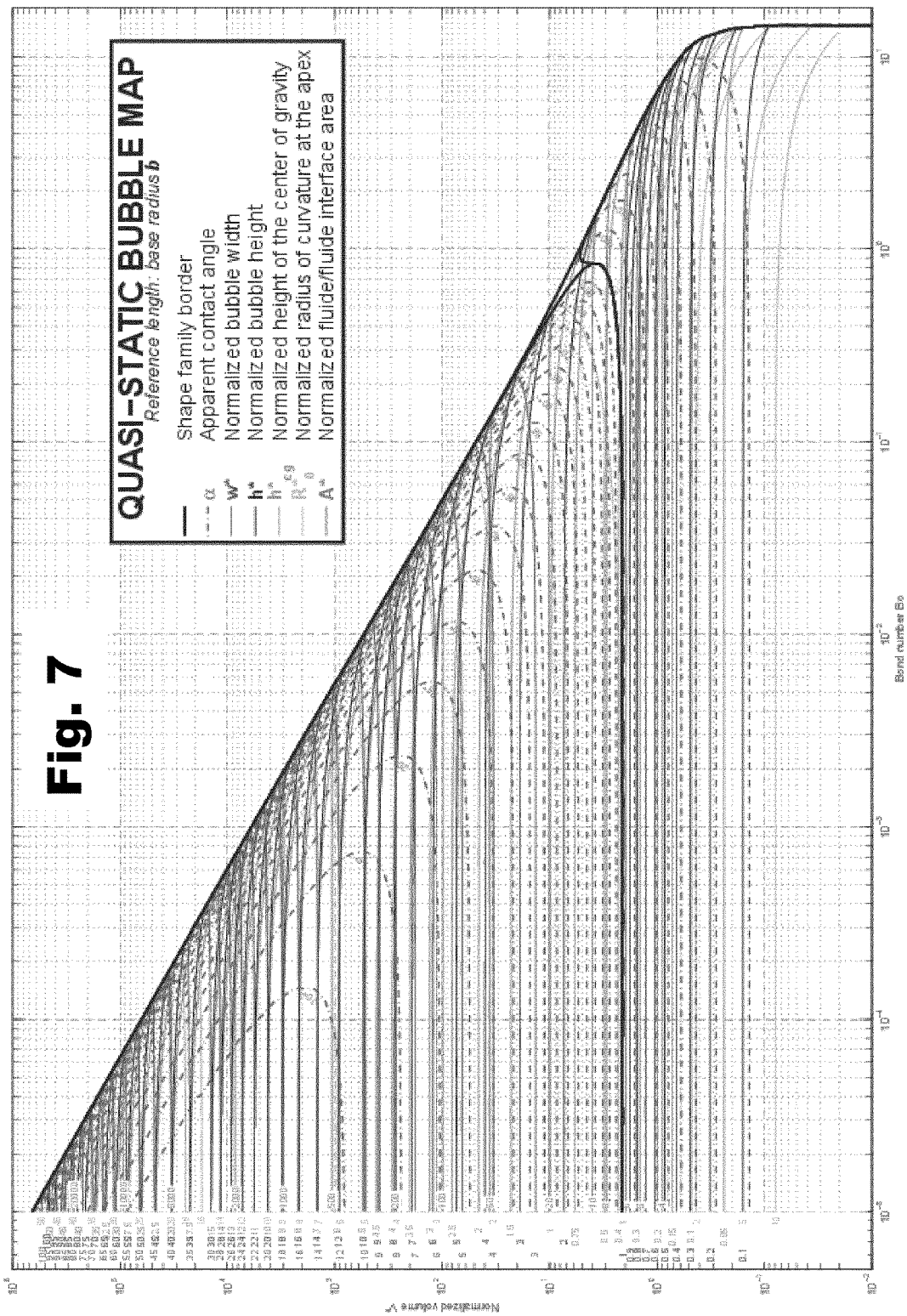
FIG. 7 is a graphical representation of a data set in which a number of parameters are plotted against Bond number (x-axis) and normalized volume (y-axis)

In this case, the mentioned equation is solved for the case of a pendant drop or bubble i.e. one which is suspended from an orifice. The key information about the bubble can be interpolated from the database using these three simple length measurements, two if the base dimension is physically fixed. In order to illustrate the database, its information is represented in FIG. 7 diagrammatically. FIG. 7 plots a number of parameters, listed in the legend box at upper right, against Bond number (x-axis) and normalized volume (y-axis). The volume is normalized against the base radius of the bubble, while the normalized bubble maximum width and height are normalized against the base radius of the bubble.

The representation of the database of solutions in FIG. 7 contains a wealth of information, which is more readily understood when represented in colour but the constraints of using a black-and-white version, as in FIG. 7, render the information less easy to readily distinguish. Accordingly, FIGS. 8 and 9 show the normalised bubble width and normalized bubble height, respectively, isolated from all of the other parameters other than the x- and y-axes.

Figure 8:
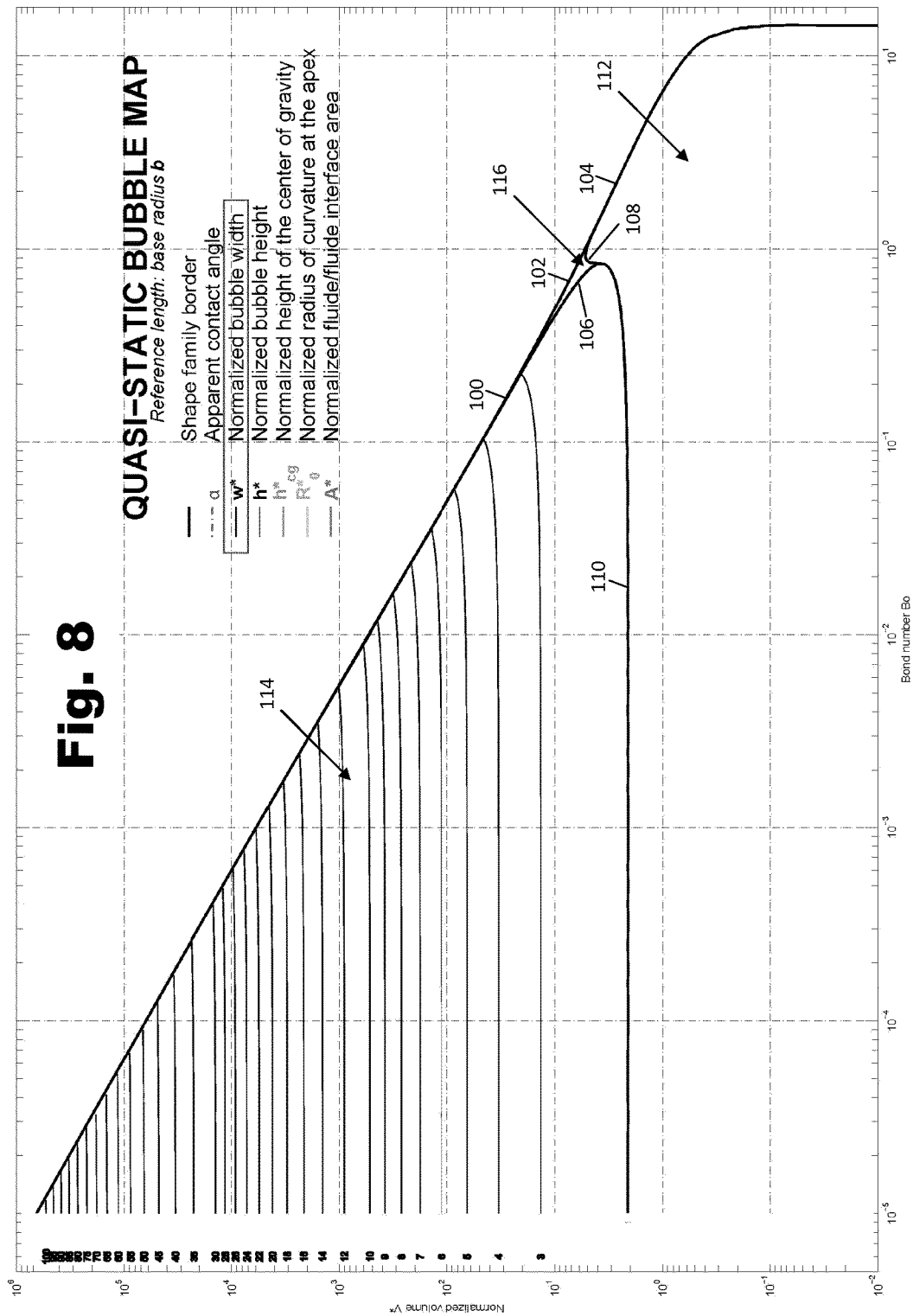
FIG. 8 is a graphical representation of a subset of the information in FIG. 7, isolating the isolines showing the normalized width of bubbles, and also showing the families of bubble shapes on this representation.

In FIG. 8, the normalized width (relative to bubble base radius) is plotted as a series of isolines. The graph can be considered a two dimensional map of bubble shapes, where each bubble, existing as a unique combination of a normalized volume and a Bond number, occupies a unique location on the map. The heavy outer boundary line 100, 102, and 104 delineates the overall area within which bubbles can stably exist. Internal boundary lines 106, 108 and 110 divide this overall area into three sub-areas, delineating between bubbles of Family 1, Family 2 and Family 3 as previously described. Family 1 bubbles exist in the large lower area 112 defined by boundaries 104, 108 and 110. Family 2 bubbles exist in the large upper area 114 defined by boundaries 100, 106 and 110. Family 3 bubbles exist in the small area 116 defined by boundaries 102, 106 and 108.

It can be seen that the isolines of bubble width are close to horizontal over much of their ranges, meaning that a given measured width will be associated with the same normalized volume for a fairly wide range of Bond numbers. However, for liquids with higher Bond numbers there is a tendency for the same width to be associated with bubbles of greater volume.

Figure 9:
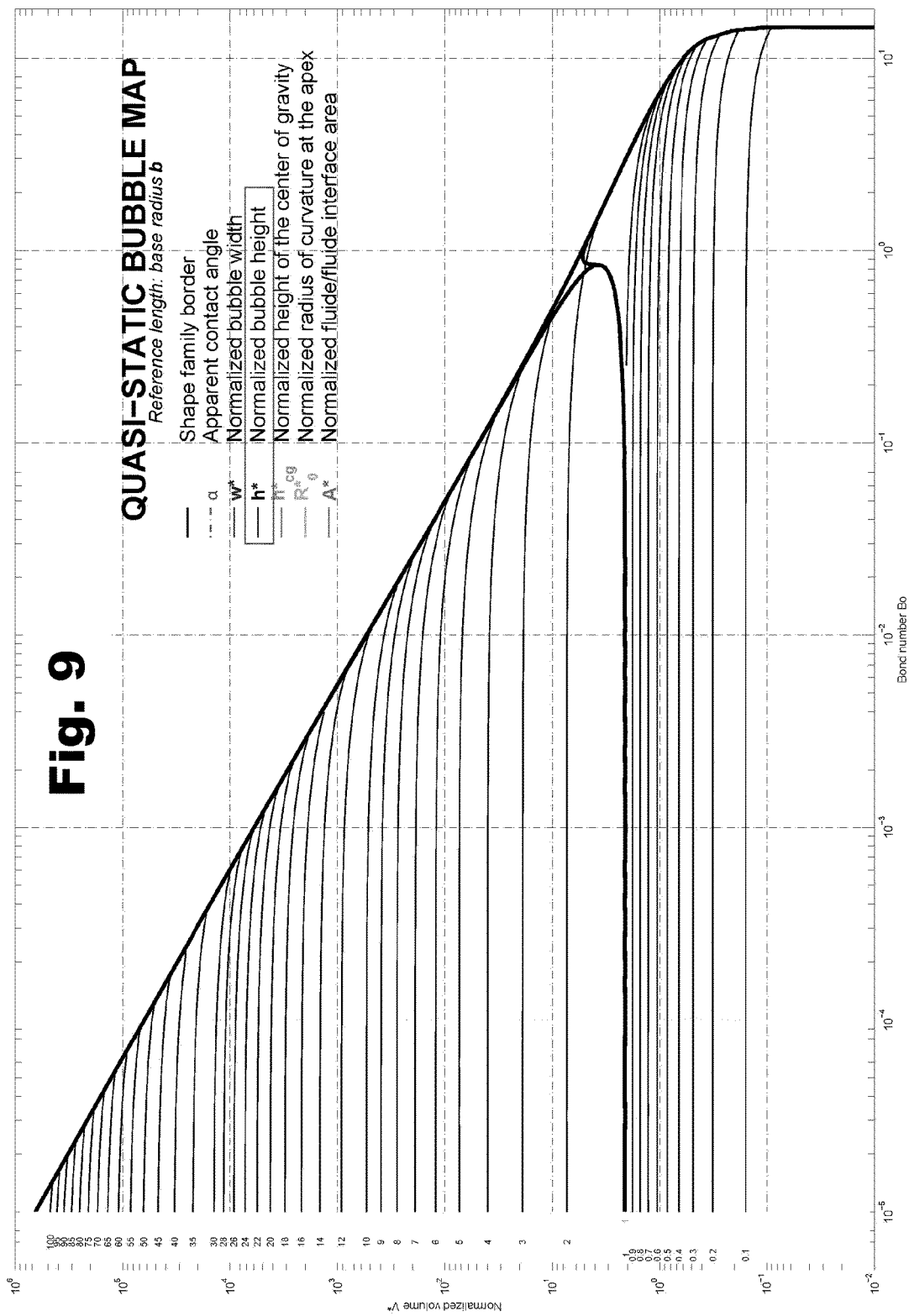
FIG. 9 is a graphical representation of a subset of the information in FIG. 7, isolating the isolines showing the normalized height of bubbles.

FIG. 9 shows the normalized bubble height, plotted in the same space. At lower Bond numbers the height is constant for a given volume, but as Bond number increases, a given height tends to be associated with a bubble of smaller volume. This can be understood, in the context of FIGS. 8 and 9 considered together, as indicating that higher Bond numbers are associated with bubbles that tend to be longer and narrower for a given volume.

Figure 10:
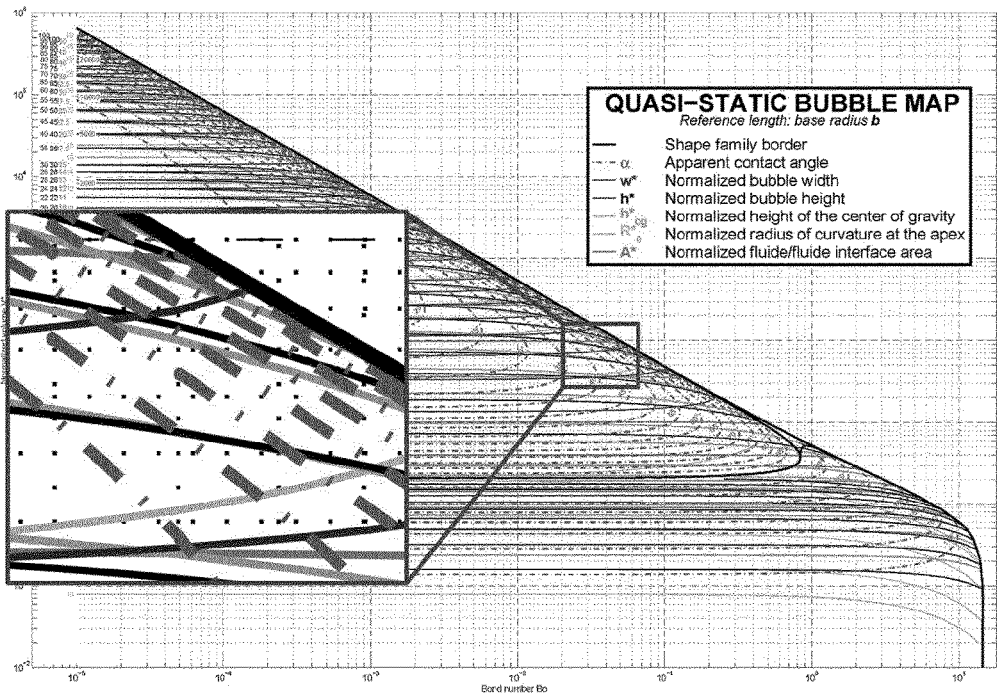
FIG. 10 is a reproduction of FIG. 7 overlaid with an exploded view of a small region of the graph.
Figure 11:
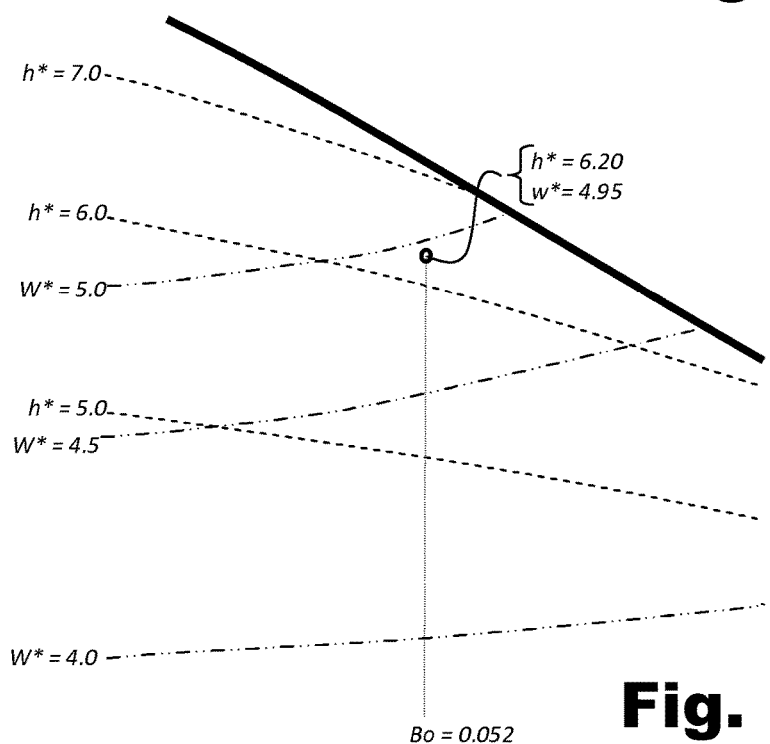
FIG. 11 is a simplified representation of the exploded region of FIG. 10, considered in terms of the two parameters of normalized width and height.

FIG. 10 shows the complete graph of FIG. 7 with an exploded region 32 in which the experimentally measured bubble is located. FIG. 11 is a simplified representation of that exploded region, considered in terms of the two parameters of normalized width and height.

It can be seen from FIG. 11 that the upward (left-to-right) tendency of the width isolines and the downward tendency of the height isolines in this region allows a combination of a measurement pair to be accurately localized.

For the experimental bubble the following linear measurements were made for width, height, and base diameter (see FIG. 3):

w=3.02 mm; h=3.78 mm; d=1.22 mm

The normalized dimensions vs. base radius are thus:

w*=2 w/d=4.95; h*=2 h/d=6.20

These two normalized parameters are sufficient to locate the bubble at a specific x-y location on the graph, as illustrated in FIG. 11. That location is at an x-axis position having a Bond number of 0.052. The Bond number is defined by the following equation:

$$B_o = \frac{d^2(\rho_l - \rho_g)g}{4\sigma}$$

Where d is the bubble base diameter, $\rho_l$ and $\rho_g$ are respectively the liquid and gas (air) densities, g is the gravitational acceleration and $\sigma$ is the surface tension. In the experimental case, g is taken to be 9.81 m·s$^{-2}$, and the density of air, $\rho_g$, is assumed to be 1 kg·m$^{-3}$. The liquid density, $\rho_l$, can be found by looking up the value for a known liquid, or by weighing a known volume. In this case it is found to be 1000 kg·m$^{-3}$.

The surface tension of the liquid can then be determined from these values in a straightforward manner:

$$\sigma = \frac{d^2(\rho_l - \rho_g)g}{4B_o}$$

$$\sigma = 70.3 \; mN/m$$

Thus, using the graph (or the underlying database) and the three simple linear measurements, together with well-known or easily found values for the densities of fluids and gravitational acceleration, the surface tension can be found.

It will be understood that the representation in the graphs of FIGS. 7-11 provide for a visual understanding of the underlying data. As described, the data values can be read directly off a graph, but one will generally obtain more accurate results by accessing the solutions in the database directly.

It will also be understood that blank areas as seen in FIG. 11 do not imply an absence of data—where a sufficient number of solutions to the underlying equation have been derived, solutions will exist in those regions lying between the isolines selected for illustration in the graph. Thus, FIG. 11 is merely an exploded region of a graph with isolines plotted at specific round numbers. The underlying database has solutions in the blank regions and has normalized heights and widths for those solutions which do not get represented on the graph (as well as all of the other derived values like contact angle, etc.). In the event that the measured values fall between values in the underlying database, conventional interpolation techniques will allow the user to readily derive the parameters associated with the interpolated solution.

Locating the bubble shape at a specific x-y location on the graph allows not only the Bond number to be derived but also each of the other plotted values which have been pre-calculated for each solution of the equation in the database. Those parameters are each plotted on a separate graph in FIGS. 12-15.

Figure 12:
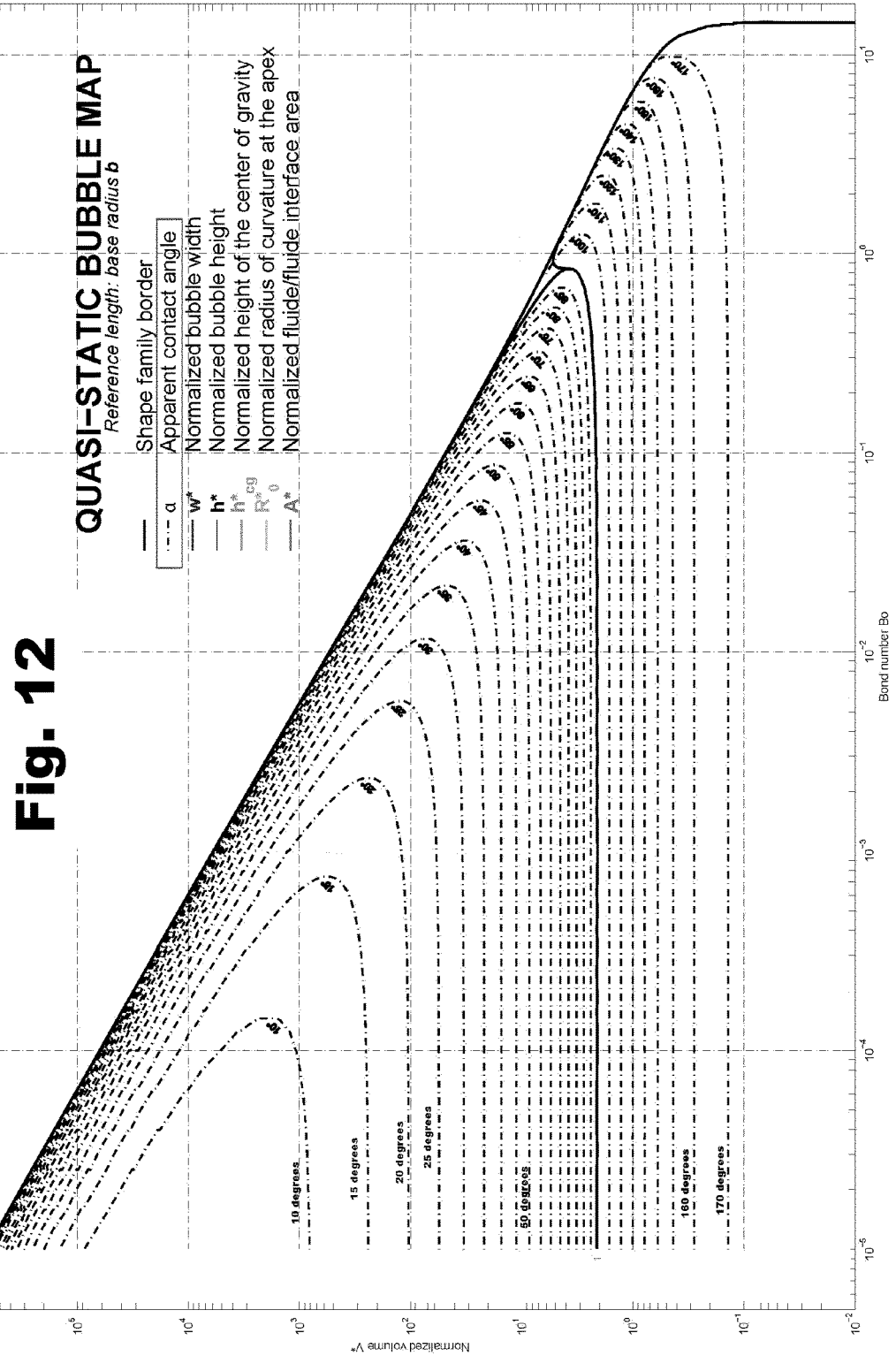
FIG. 12 is a graphical representation of a subset of the information in FIG. 7, isolating the isolines showing the apparent contact angle.

FIG. 12 shows the apparent contact angle, $\sigma$, which is plotted as a series of isolines or contour lines of constant contact angle in the two-dimensional landscape of normalized volume V* vs Bond number Bo. It can be seen that the contact angles exhibit much greater resolution in some regions of the graph than was seen for the height and width values. So for a normalized volume V* of $10^{-4}$, a bubble with a contact angle of 10° will imply a Bond number of about $7 \times 10^{-5}$, whereas a contact angle of 15° would imply a Bond number of slightly more than $1 \times 10^{-4}$, for the same normalized volume of $10^{-4}$. Again, solutions also exist in the rather large region between 10° and 15° and while the graph appears blank, the database is fully populated with solutions for contact angles of 11°, 12°, 13° and 14° and also for intermediate, non-integer values.

Figure 13:
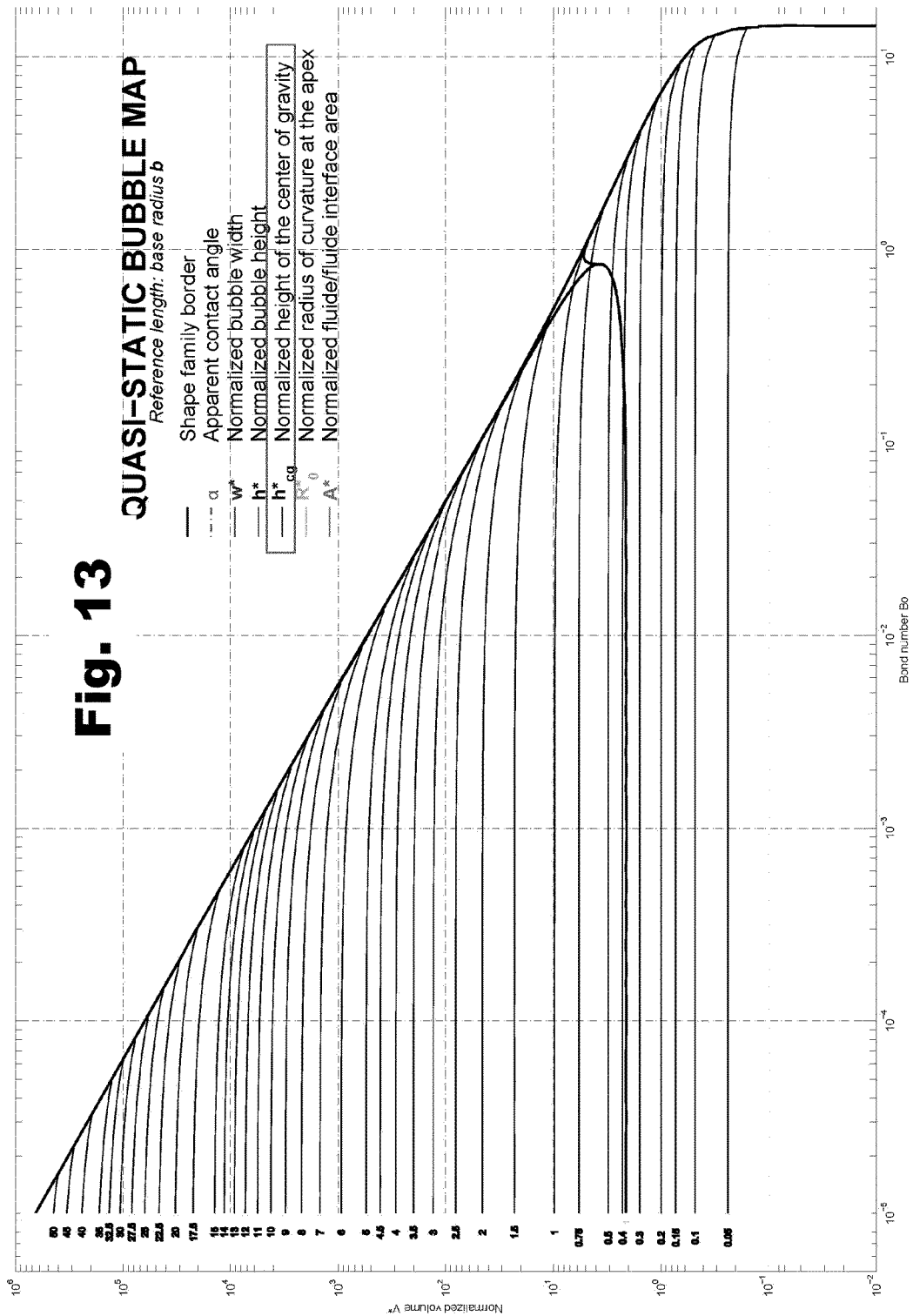
FIG. 13 is a graphical representation of a subset of the information in FIG. 7, isolating the isolines showing the normalized height of the centre of gravity.
Figure 14:
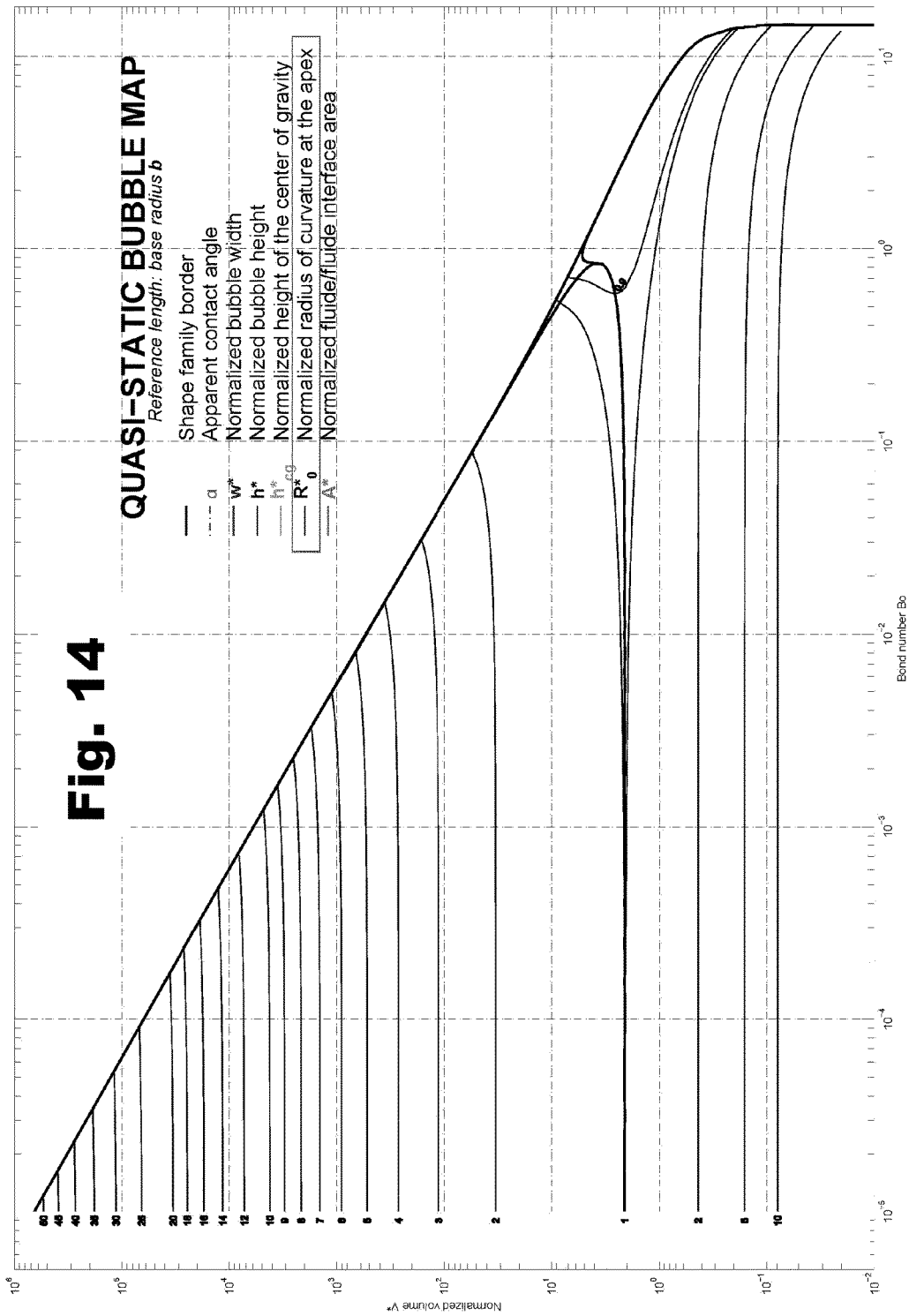
FIG. 14 is a graphical representation of a subset of the information in FIG. 7, isolating the isolines showing the radius of curvature at the apex.
Figure 15:
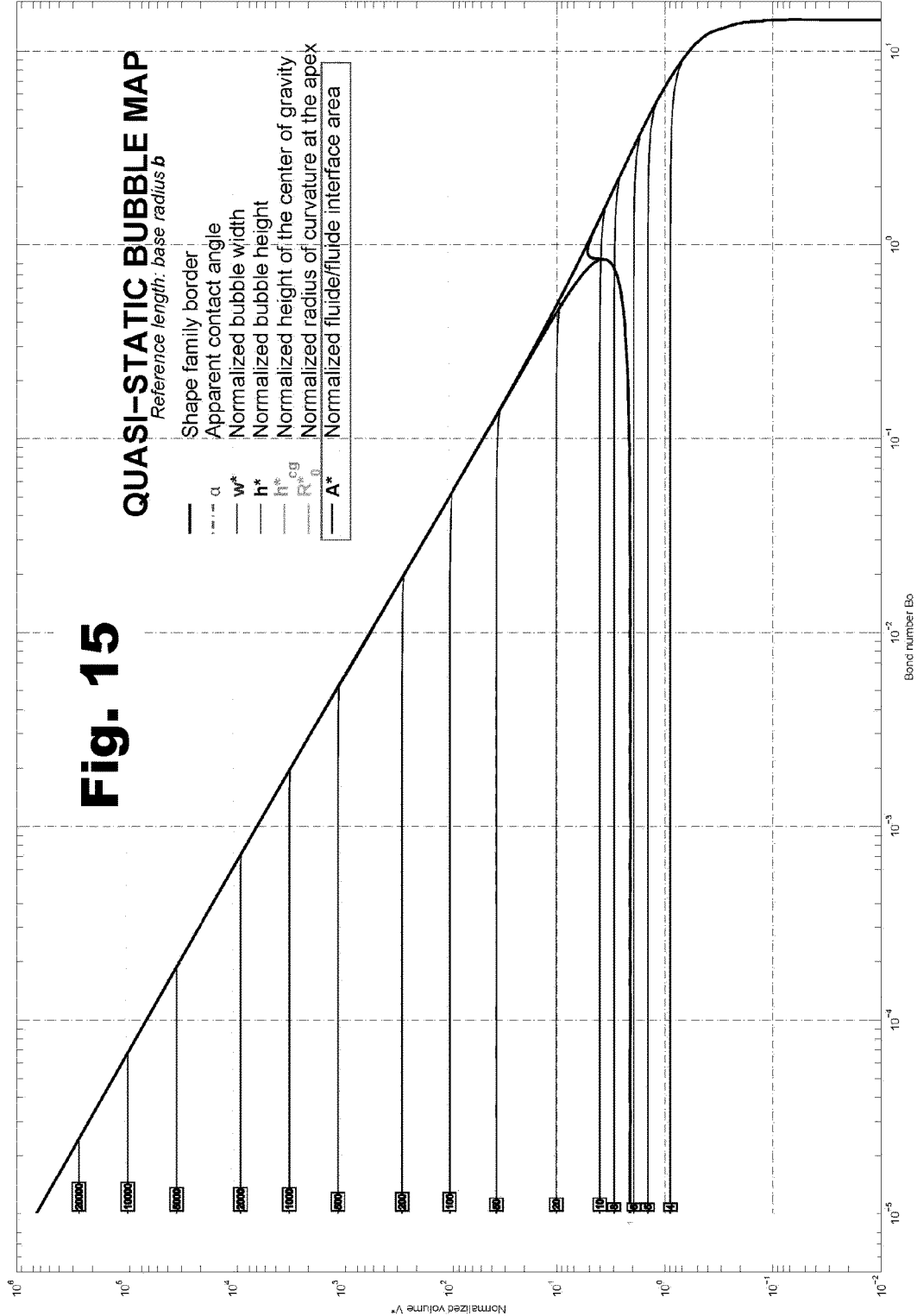
FIG. 15 is a graphical representation of a subset of the information in FIG. 7, isolating the isolines showing the total interface area.

FIGS. 13, 14 and 15 show the remaining parameters of the FIG. 7 graph, isolated from the other parameters and plotted in the same space, namely the normalized height of the centre of gravity (FIG. 13), the radius of curvature at the apex (FIG. 14) and the total interface area (FIG. 15). For each of these parameters, the location of a bubble shape at a specific x-y position in the 2D space of normalized volume vs. Bond number, allows the skilled person to read off or interpolate the associated value for the parameter in question.

Thus one may solve a very large number of solutions of the governing equation, and store relevant geometric features of these solutions in a database. Then, keeping the example of the surface tension measurement, it is only necessary to measure simple dimensions of the drop (or bubble) such as its height, maximum width and base width, in order to interpolate from the data in the database the value of its surface tension. This innovative method avoids the necessity to fit a mathematical solution to the entire drop contour by solving all possible solutions of the equation a priori. It results in a simpler, faster measurement, with the possibly of much improved accuracy.

The same method can be used in order to measure the bubble (or drop) volume, the height of its centre of gravity, its interface area, the radius of curvature at its apex or any geometrical feature, including the apparent contact angle at the base of the bubble or drop. This is particularly useful to characterize the wettability property of a fluid on a given surface. In the case of contact angle, it is more appropriate to use a sessile bubble (or drop) on (or below) a horizontal flat surface. The governing equation that would describe such a bubble/drop would still be equation 1, but with a negative value for the gravitational acceleration.

The database and graphs of FIGS. 7-15 are complex because they capture a great deal of information for each bubble shape solution. It is possible to maintain instead a more simplified database, or to represent the database as a simpler data set, if one wishes to perform only a specific look-up operation.

Figure 16:
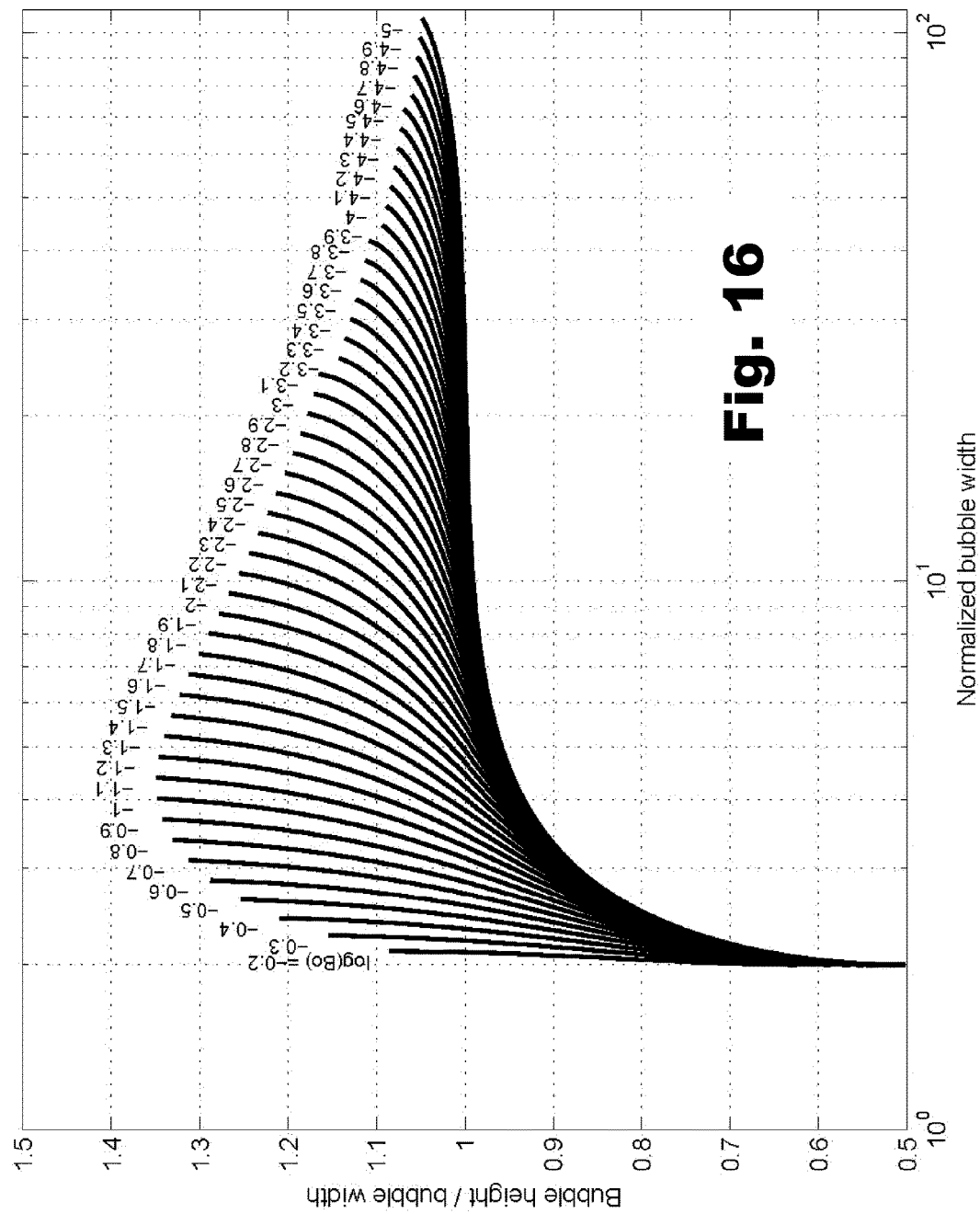
FIG. 16 is a plot of Bond number isolines against normalised width on the x-axis, and against the ratio of a bubble's height to its width on the y-axis.

For example, FIG. 16 is a graph tailored to the first operation discussed earlier—taking a bubble's height, width and base diameter, and finding the Bond number which is associated with this combination. FIG. 16 plots the normalised width w* on the x-axis, and on the y-axis, plots the ratio of the bubble's height to its width. These two axes thus capture the three linear measurements for a given experimental bubble. The two-dimensional space thus created is populated with Bond number logarithmic isolines.

Thus, by measuring the values for w, h and d as previously described, and by calculating the quantities h/w and 2 w/d, a simple lookup will give the isoline value that overlies the identified point. In the case of the experimental bubble discussed earlier, the y-axis value is 1.252 and the x-axis value is again 4.95. The Isoline value at this point is −1.28, which is $\log_{10}(0.052)$. This simple lookup allows a very rapid calculation of Bond number from three measurements that can be made easily and with great accuracy.

The accuracy of the graphical method was compared against the leading existing techniques and against theory as follows. A gas bubble is created in water from a 1.22 mm diameter orifice located in a horizontal, upward-facing surface immersed in quiescent water in terrestrial gravity conditions. (This is basically the bubble pictured in FIGS. 2 and 3.)

The volume of gas introduced into the bubble was measured at 17.78 mm$^3$, and the capillary length of water has a known value of 2.7 mm. Consequently, the bubble base radius is b=0.61 mm, the Bond number value is Bo=0.052 and the normalized volume is $V_b^*$=78.3.

Figure 21:
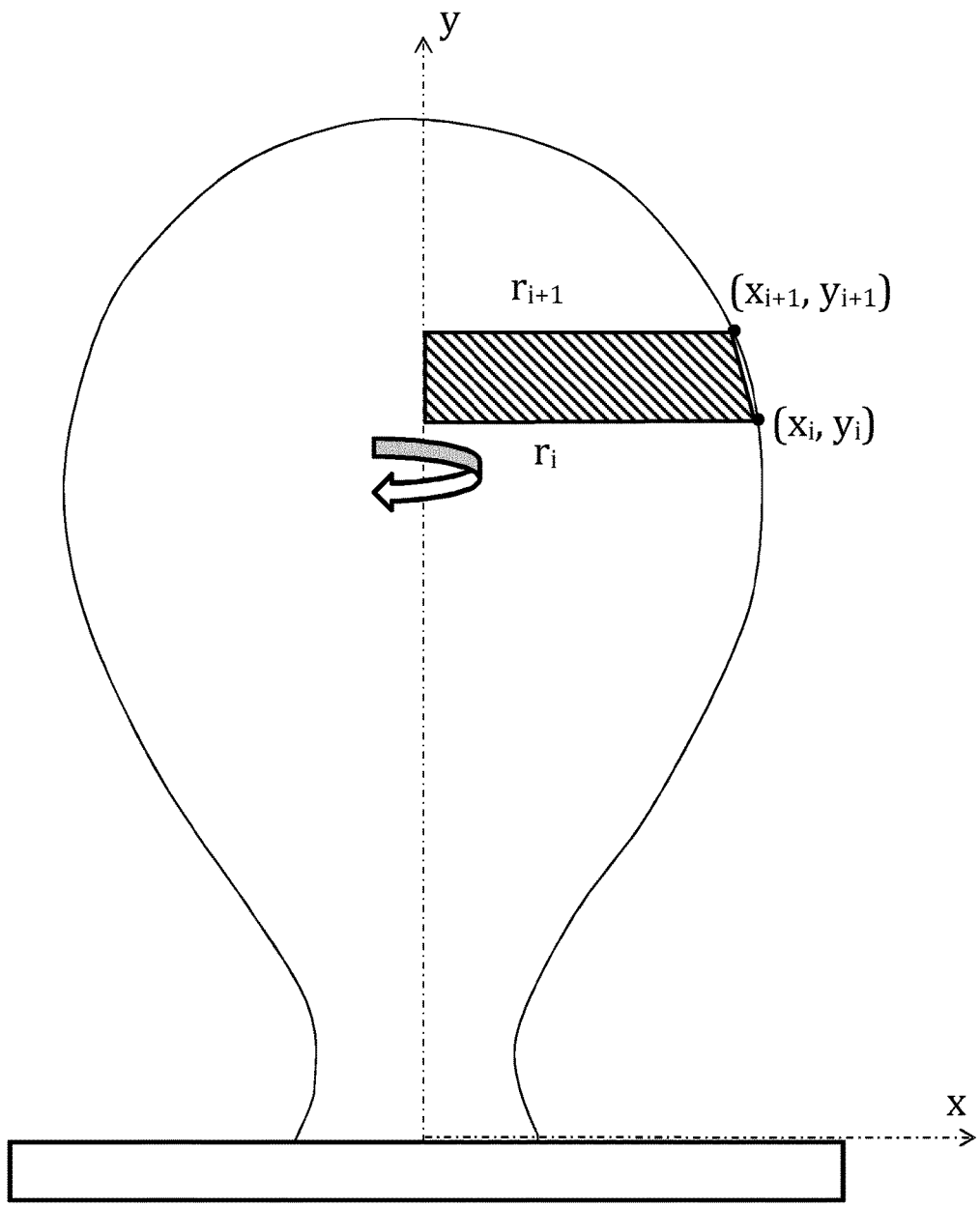
FIG. 21 is a diagram illustrating an image processing technique for measuring bubble or drop volume.

In order to find the "true" volume for the purposes of comparing different approaches, the following technique was used. The volume was calculated by imaging the bubble with a high resolution photo, using the pixel locations on the interface and then revolving to create layers of 3D disks (with bevelled edges) and then adding the subsequent volumes to get the total bubble volume ($V_b$=17.78 mm$^3$). The normalized volume is $V_b^*=V_b/b^3$. FIG. 21 illustrates this technique, showing two edge pixels located at positions ($x_i$, $y_i$) and ($x_{i+1}$, $y_{i+1}$) defining a quadrilateral area (shaded) which when rotated 360 degrees about the y-axis will result in a disc volume with a bevelled outer edge. Summing the volumes of all such discs with a suitably small incremental height between successive edge pixels (this increment is obviously exaggerated in FIG. 21 for clarity), gives a measurement of the bubble volume.

As a first set of data for comparison, the dimensions of the bubble (normalized height, normalized width, normalized height of centre of gravity, and apparent contact angle) can be measured from the photographic image of the bubble.

Figure 17:
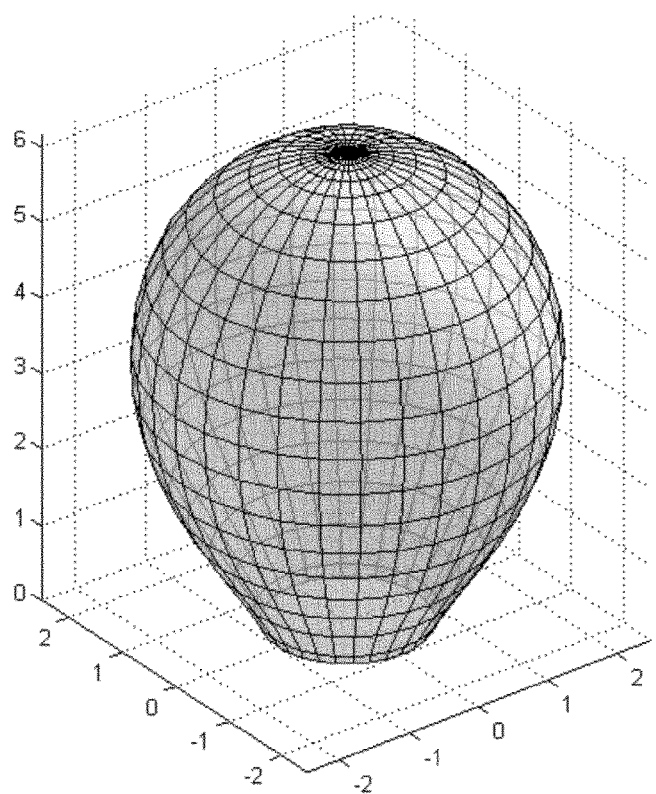
FIG. 17 is a graphical model of a bubble, obtained as a solution to the Laplace equation.

As a second set of data, a normalized solution to the Laplace equation is calculated based on the known parameters to obtain a model of the resultant bubble, which is illustrated in FIG. 17. From that model or simulation, numerical values can be obtained for the same four dimensions (normalized height, normalized width, normalized height of centre of gravity, and apparent contact angle) as well as the normalized total interface area, A*, and the radius of curvature at the apex, $R_0^*$.

As a third set of data, we have the data from the database underlying the graph of FIG. 7. Using the normalized volume and the known Bond number, the x-y position of the bubble can be localised on the graph (see FIG. 10) and the value of each of the plotted parameters at that x-y position can be read from the graph, to give a set of values for the same parameters as with the second set of data.

TABLE 1

Comparison of the estimation of geometrical properties by experimental (photographic) determination, contour simulation and use of the graph of FIG. 7

|  | Experimental | Simulated model | Read from graph |
| --- | --- | --- | --- |
| h* | 6.20 | 6.20 | 6.2 |
| w* | 4.98 | 4.96 | 4.95 |
| $h_{cg}^*$ | 3.29 | 3.23 | 3.25 |
| α | 64° | 65° | 65° |
| A* | — | 87.2 | 85 |
| $R_0^*$ | — | 2.35 | 2.3 |

Table 1 sets out the comparative numerical values. It can be seen that a very good agreement is found between the three different methods as all values present less than 3% discrepancy.

Figure 18:
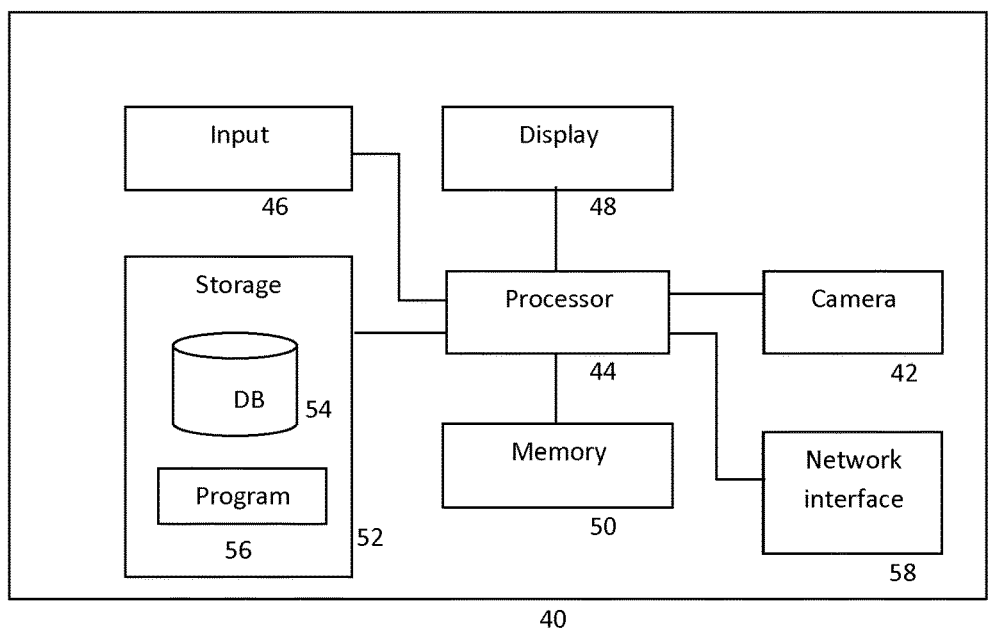
FIG. 18 is a block diagram of a computing device.

The method can be implemented in computer code running on a computing device. An example of such a device is illustrated in block diagram form in FIG. 18. The device 40 of FIG. 18 can be any suitable computing device but preferably is a smartphone, tablet, or similar handheld device (including a dedicated scientific instrument). A camera 42 is provided to capture an image of a bubble 44 under the control of a suitable input interface 46. A display 48 allows the user to see the captured image which is stored typically in a working memory 50 temporarily, and in a non-volatile storage unit 52 permanently. It will be understood that devices having this functionality to capture images of a reasonably high resolution are ubiquitous.

The functionality need not all be carried on-board a single device. The image of a bubble or droplet can equally be captured by an external imaging system such as a digital camera or CCD disposed as part of a measurement apparatus, with a connection to the computing device.

The storage means 52 also has a database 54 within which data, representing multiple solutions to the equation describing the shape of a bubble or droplet, are stored. Such data typically is organised in a manner that allows a look-up of a solution based on a limited number of dimensional input parameters, such as a combination of two or three linear measurements of a bubble or droplet (or a composite parameter like a measurement of one dimension of the bubble, normalized with respect to another measurement). The data stored for each solution can be one or more complex parameters of the shape of bubble described by the solution, including without limitation the Bond number (or a similar characteristic of the system), surface tension, contact angle, volume, area, height of centre of gravity, radius of curvature, or parameters of the curvature itself. Thus, the database allows the look-up of complex parameters from simple linear measurements.

Also stored within the storage unit 52 is program code 56 which specifies the steps to be taken in extracting the features from an image, and deriving from the database the desired complex parameters. A network interface, such as is known in conventional mobile phones and tablets, allows communication from and to the device.

The program code is preferably in the form of an "app" or downloadable program, in the case of the device 40 being a mobile phone or tablet.

Figure 19:
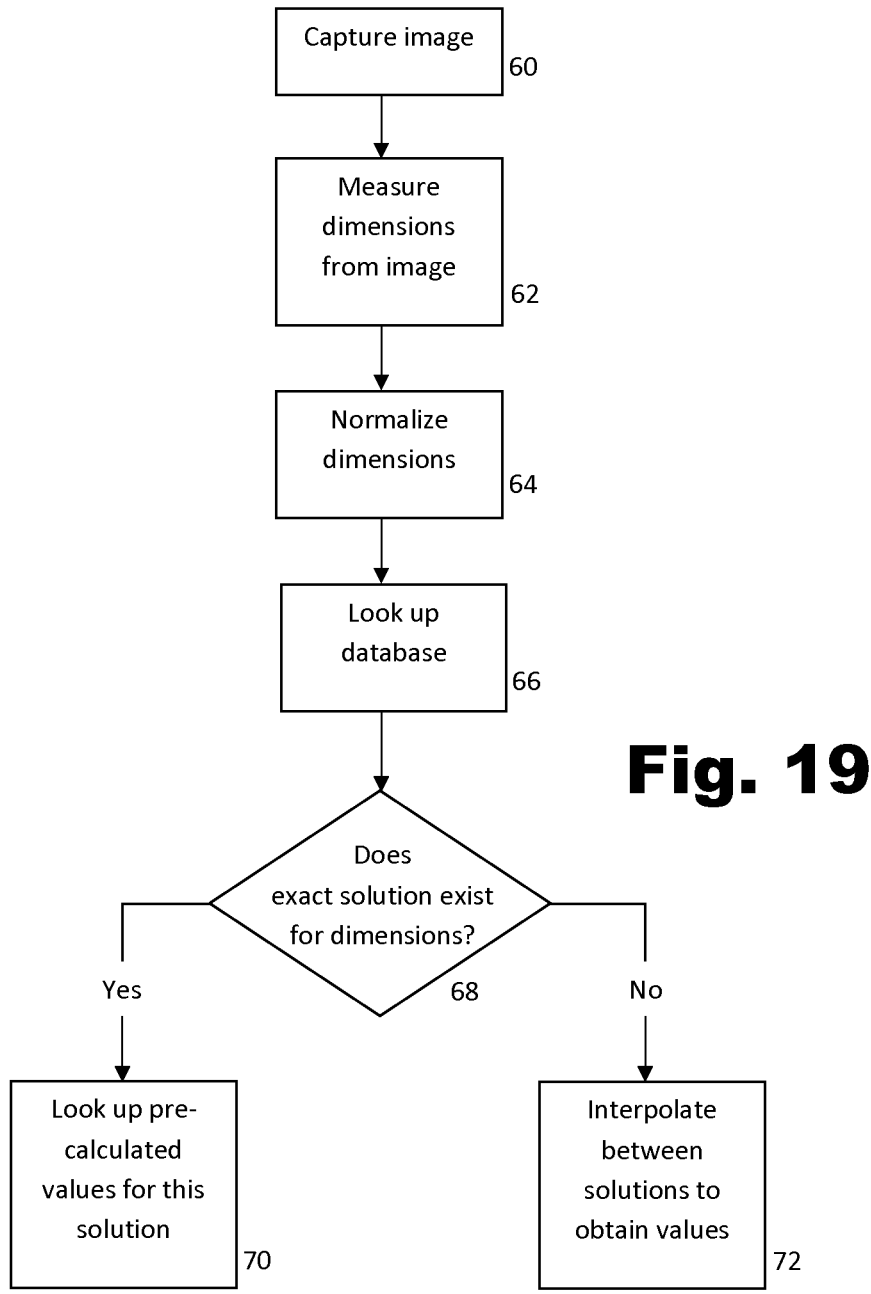
FIG. 19 is a flowchart of program code.

FIG. 19 is a flowchart of the program code. In step 60 an image is captured by the camera in response to a user input. Thus, a user will typically launch the program, which will in turn provide a camera view on-screen. The user will position the camera to obtain a good bubble or droplet image (i.e. one which fills the screen as far as practical and has clearly defined edges), then select shutter operation. The image from the camera sensor is typically pre-processed and stored in memory as well as being copied onto the permanent storage (such as an internal or external memory card).

Image processing in the software then measures the dimensions of the image, step 62, by performing a conventional edge detection to determine the edges of the droplet or bubble, straightening the image according to a reference axis (such as the axis of symmetry of the bubble or a reference edge visible in the image), and then measuring the length of predetermined dimensions, such as bubble height, maximum width, and width at the connection point to a surface (or base diameter). The measured dimensions can be determined in terms of numbers of pixels across each dimension, or converted to actual estimated lengths e.g. in mm, according to depth cues or assumed distance from the bubble.

Alternative, and indeed improved, methods can equally be used to capture linear dimensions, and the technique encompasses such methods. A limitation in the use of a camera or CCD is that accuracy is restrained to the pixel resolution of the image.

In one improvement, the camera is omitted and instead dimensions are captured using laser interferometry. For example, if the drop height, width and base diameter are measured by displacing a laser beam, and measuring when the beam is intercepted by the drop, then two advantages arise for an enhanced accuracy:

The parallax error inherent in camera imaging with a single lens position is suppressed The accuracy of the linear measurement can be perhaps 1000 times than the best achievable pixel resolution.

In step 64, the dimensions are normalized by the processor. In the preferred method, the base diameter or radius is used to normalize the width and height. However, this need not be the case, and any of these dimensions can be normalized against any of the others. For example, in the FIG. 16 example, the normalized dimensions were width relative to base radius, and height relative to width.

In step 66, the program accesses the database 54 to look up solution values which correspond to the dimensions as measured and normalized. Depending on the granularity of the database, the resolution of the image, and the degree of rounding when normalizing, the exact values used to look up the database index may or may not be present. Accordingly, in decision 68, a determination is made if the values are present for a direct look up.

If so, step 70, then the pre-calculated values are determined for the solution that corresponds to the normalized linear dimensions. If not, a suitable interpolation routine is employed in step 72 to obtain values that are deemed to be a best match.

The retrieved or interpolated parameters can include items such as the Bond number, from which the surface tension can be calculated when the densities of the liquid and gas are known (and assuming standard gravity or some adjusted accelerating field). Post-processing steps may therefore allow the user to input additional values and obtain derived properties like surface tension, wettability, or any other property that can be derived or calculated from the values retrieved from the database.

Figure 20:
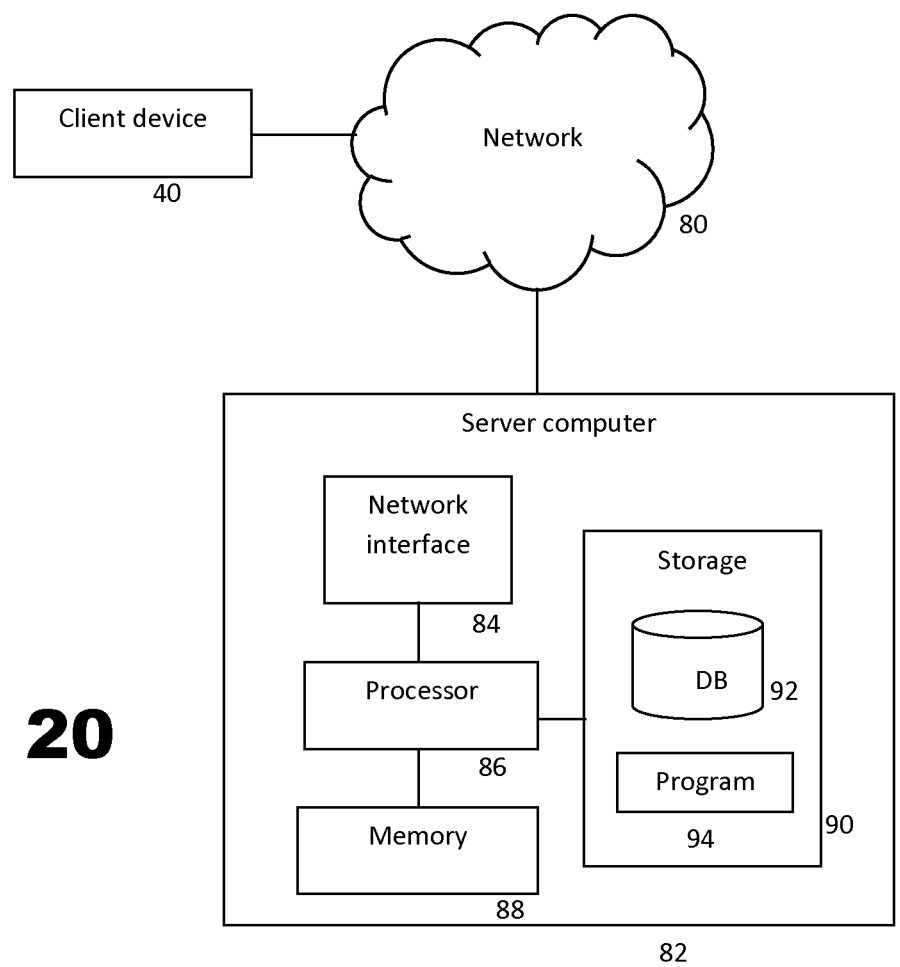
FIG. 20 is a block diagram of a distributed architecture.

FIG. 20 illustrates a distributed architecture, in which the device 40 is connected via a local area network or wide area network like the Internet 80 to a server computer 82. The device 40 in this case is modified relative to the device shown in FIG. 18 as follows: rather than carrying the full set of program instructions and the database 54 in its storage 52, it carries a set of program instructions for a more limited subset of the functions as will be described below, and the database is not carried internally within device 40, but rather is stored as a database 92 within storage 90 accessible by the server.

The server 82 has a network interface 84, a processor 86, working memory 88, and the aforementioned non-volatile storage medium 90. It also carries program instructions 94 relating to its part of the functionality of the method in this client-server relationship.

In one implementation, the program instructions at the device are limited to capturing the image and sending the image to the server computer over the network, with the server computer's program causing the server to analyse the image, obtain the dimensional values, look up the database 92, and return as an output whatever values are sought by the device 40 for display to the user.

In another implementation, the device carries out the image processing and the extraction of the dimensions, and simply transmits these to the server for look-up of the stored complex parameters of an appropriate solution in the database. The skilled person will appreciate that the distributed nature of computing solutions allows many other variations in the configuration of a suitable computer system, enabling measurements of a droplet to be converted to useful complex parameters of the droplet, based on the common factor of having a pre-calculated family of solutions describing different candidate droplets to which the dimensional measurements can be fitted to select an appropriate solution.

The invention claimed is:

1. A method of determining the properties of a fluid body in the form of a surface-attached droplet/bubble, the method comprising:
   (a) storing, in a memory accessible by a processing apparatus, a set of data describing a plurality of droplets/bubbles of different shapes, wherein each shape is captured in said data set as a combination of two or more linear dimensional measurements, and wherein for each shape the data set includes one or more parameters describing the relationship between the physical properties of a pair of fluids capable of forming said shape when a first of said fluids is a surface-attached droplet/bubble disposed in a surrounding medium of the second of said fluids;
   (b) providing a fluid body as a surface-attached droplet/bubble of a first fluid in a surrounding medium of a different second fluid;
   (c) measuring a plurality of linear dimensional measurements of said fluid body;
   (d) providing said measurements as an input to a processing apparatus; and
   (e) said processing apparatus determining from said data set said one or more parameters associated with the shape described by said linear dimensional measurements; and
   (f) providing the determined one or more parameters;
   wherein the two or more linear dimensional measurements are normalised measurements, the two or more linear measurements are normalised against a further linear measurement of the bubble/drop, and the further linear measurement is a base diameter or base radius of the bubble drop at a surface to which it is attached.

2. The method of claim 1, wherein one of the first and second fluids is known and the other is unknown, and wherein the properties of the known fluid permit the derivation from said one or more parameters of corresponding properties of the unknown fluid.

3. The method of claim 1, wherein said one or more parameters comprise a parameter which is a function of an accelerating field, a surface tension of one fluid at the interface with the other fluid, and the respective fluid densities.

4. The method of claim 3, wherein the accelerating field is the local gravitational field as characterised by the acceleration due to gravity, g.

5. The method of claim 1, wherein the two or more linear dimensional measurements of the data set comprise any two of the following measurements normalised against the remaining measurement: height normal to attachment surface, maximum width parallel to attachment surface, and base diameter/radius at attachment surface.

6. The method of claim 1, wherein the two or more linear dimensions of the data set are expressed as a combination of dimensions such as an area or a volume.

7. The method of claim 1, wherein the data set is limited based on one or more of the following assumptions used to create the data set:
   (a) a value for one or more properties of the first fluid;
   (b) a value for one or more properties of the second fluid;
   (c) a value for one or more properties of the interface between first and second fluids,
   (d) a value for an acceleration such as gravitational acceleration, g.

8. The method of claim 1, wherein said set of data comprises a plurality of parameter sets, each parameter set describing a unique solution to an equation modelling the shape of a droplet/bubble, and each parameter set including said combination of two or more linear dimensional measurements and said one or more parameters describing the relationship between the physical properties of a pair of fluids capable of providing said solution.

9. A method of determining the properties of a fluid body in the form of a surface-attached droplet/bubble, the method comprising:
   (a) storing, in a memory accessible by a processing apparatus, a set of data describing a plurality of droplets/bubbles of different shapes, wherein each shape is captured in said data set as a combination of two or more linear dimensional measurements, and wherein for each shape the data set includes one or more parameters describing the relationship between the physical properties of a pair of fluids capable of forming said shape when a first of said fluids is a surface-attached droplet/bubble disposed in a surrounding medium of the second of said fluids;
   (b) providing a fluid body as a surface-attached droplet/bubble of a first fluid in a surrounding medium of a different second fluid;
   (c) measuring a plurality of linear dimensional measurements of said fluid body;
   (d) providing said measurements as an input to a processing apparatus; and
   (e) said processing apparatus determining from said data set said one or more parameters associated with the shape described by said linear dimensional measurements;
   wherein the two or more linear dimensional measurements are normalised measurements, the two or more linear measurements are normalised against a further linear measurement of the bubble/drop, and the further linear measurement is a base diameter or base radius of the bubble drop at a surface to which it is attached;
   wherein a bubble of said gas in said liquid or a droplet of said liquid in said gas is used in step (b),
   wherein the resultant shape of the bubble/droplet is encompassed within the data set in step (a),
   wherein the one or more parameters describing the relationship between the physical properties of a pair of fluids include at least one parameter based on interfacial surface tension, said at least one parameter being determined in step (e).

10. A non-transitory computer program product comprising instructions encoded on a data carrier which, when executed in a computing system, implement operations that comprise:
   (a) receive as an input a plurality of linear dimensional measurements of a droplet/bubble;
   (b) access a memory storing a set of data describing a plurality of droplets/bubbles of different shapes, wherein each shape is captured in said data set as a combination of two or more linear dimensional measurements, and wherein for each shape the data set includes one or more parameters describing the relationship between the physical properties of a pair of fluids capable of forming said shape when a first of said fluids is a surface-attached droplet/bubble disposed in a surrounding medium of the second of said fluids;

(c) determining from said data set said one or more parameters associated with the shape described by said linear dimensional measurements received as an input; and (d) providing as an output said one or more parameters;

wherein the two or more linear dimensional measurements are normalised measurements, the two or more linear measurements are normalised against a further linear measurement of the bubble/drop, and the further linear measurement is a base diameter or base radius of the bubble drop at a surface to which it is attached.

11. An apparatus for determining the properties of a fluid body in the form of a surface-attached droplet/bubble, comprising:
(a) a memory storing a set of data describing a plurality of droplets/bubbles of different shapes, wherein each shape is captured in said data set as a combination of two or more linear dimensional measurements, and wherein for each shape the data set includes one or more parameters describing the relationship between the physical properties of a pair of fluids capable of forming said shape when a first of said fluids is a surface/bubble disposed in a surrounding medium of the second of said fluids;
(b) a processor programmed to receive as an input, a plurality of linear dimensional measurements of a fluid body as a surface-attached droplet/bubble of a first fluid in a surrounding medium of a different second fluid providing said measurements as an input to a processing apparatus; and
(c) a program causing said processor to determine from said data set said one or more parameters associated with the shape described by said linear dimensional measurements, wherein the two or more linear dimensional measurements are normalised measurements, the two or more linear measurements are normalised against a further linear measurement of the bubble/drop, and the further linear measurement is a base diameter or base radius of the bubble drop at a surface to which it is attached.

12. The apparatus as claimed in claim 11, further comprising a measurement system for making said plurality of linear dimensional measurements, and an output therefrom to said processor.

13. The apparatus of claim 11, wherein one of the first and second fluids is known and the other is unknown, and wherein the properties of the known fluid permit the derivation from said one or more parameters of corresponding properties of the unknown fluid.

14. The apparatus of claim 11, wherein said one or more parameters comprise a parameter which is a function of an accelerating field, a surface tension of one fluid at the interface with the other fluid, and the respective fluid densities.

15. The apparatus of claim 14, wherein the accelerating field is the local gravitational field as characterised by the acceleration due to gravity, g.

16. The apparatus of claim 11, wherein the two or more linear dimensional measurements of the data set comprise any two of the following measurements normalised against the remaining measurement: height normal to attachment surface, maximum width parallel to attachment surface, and base diameter/radius at attachment surface.

17. The apparatus of claim 11, wherein the two or more linear dimensions of the data set are expressed as a combination of dimensions such as an area or a volume.

18. The apparatus of claim 11, wherein the data set is limited based on one or more of the following assumptions used to create the data set:
(a) a value for one or more properties of the first fluid;
(b) a value for one or more properties of the second fluid;
(c) a value for one or more properties of the interface between first and second fluids;
(d) a value for an acceleration such as gravitational acceleration, g.

19. The apparatus of claim 11, wherein said set of data comprises a plurality of parameter sets, each parameter set describing a unique solution to an equation modelling the shape of a droplet/bubble, and each parameter set including said combination of two or more linear dimensional measurements and said one or more parameters describing the relationship between the physical properties of a pair of fluids capable of providing said solution.

* * * * *